United States Patent [19]

Martin et al.

[11] Patent Number: 5,135,599
[45] Date of Patent: Aug. 4, 1992

[54] METHOD OF MAKING A TRIPLE LUMEN CATHETER

[75] Inventors: Geoffrey S. Martin; Michael R. LeBlanc, both of Mississauga, Canada

[73] Assignee: Vas-Cath Incorporated, Mississauga, Canada

[21] Appl. No.: 699,421

[22] Filed: May 13, 1991

Related U.S. Application Data

[62] Division of Ser. No. 288,364, Dec. 22, 1988.

[30] Foreign Application Priority Data

Dec. 22, 1987 [CA] Canada .................. 555076

[51] Int. Cl.⁵ .................. B32B 31/00; A61M 3/00
[52] U.S. Cl. .................. 156/294; 264/322; 604/43; 604/280
[58] Field of Search .................. 604/39–46, 604/164–169, 264, 280, 283, 284; 264/322; 156/294, 60, 198, 293, 304.2, 304.5, 304.6, 308.2

[56] References Cited

U.S. PATENT DOCUMENTS

| | | | |
|---|---|---|---|
| 3,528,869 | 9/1970 | Dereniuk | 156/294 |
| 3,634,924 | 1/1972 | Blake et al. | 29/447 |
| 4,072,146 | 2/1978 | Howes | 128/205 |
| 4,168,703 | 9/1979 | Kenigsberg | 604/280 |
| 4,251,305 | 2/1981 | Becker et al. | 604/103 |
| 4,390,383 | 6/1983 | van Dongeren | 156/294 |
| 4,406,656 | 4/1983 | Hattler et al. | 604/280 |
| 4,583,968 | 4/1986 | Mahurkar | 604/280 |
| 4,668,225 | 5/1987 | Russo et al. | 604/280 |
| 4,670,009 | 6/1987 | Bullock | 604/280 |
| 4,681,564 | 7/1987 | Landreneau | 604/280 |
| 4,769,005 | 9/1988 | Ginsburg et al. | 604/164 |
| 4,813,429 | 3/1989 | Eshel et al. | 604/43 |
| 4,961,809 | 10/1990 | Martin | 603/280 |
| 4,968,307 | 11/1990 | Dake et al. | 604/280 |

Primary Examiner—C. Fred Rosenbaum
Assistant Examiner—Mark W. Bockelman
Attorney, Agent, or Firm—Rogers & Scott

[57] ABSTRACT

A method of manufacturing a multiple lumen catheter with a tapered tip and an end aperture concentric with the main catheter body is described. The method includes providing a flexible elongate body extending about a longitudinal axis having a distal end, a proximal end, an outer wall, a septum extending between spaced points on the outer wall to define first and second lumens, and a third lumen defined about said axis in a central portion of the septum. A straight wire is inserted into the third lumen to project centrally from the distal end of the body and the distal end of the body is then inserted into a tapering mould having a centrally located aperture to receive the wire. The distal end of the body is softened in the mould such that the distal end deforms to a tapered shape with the outer wall of the body merging with the septum to close the first and second lumens. Openings are then formed in the outer wall communicating with the first and second lumens adjacent the distal end.

3 Claims, 9 Drawing Sheets

METHOD OF MAKING A TRIPLE LUMEN CATHETER

This application is a division of application Ser. No. 07/288,364 filed on Dec. 22, 1988 still pending.

This invention relates to a method of making a multiple lumen catheter and more particularly to a method of making such a catheter for insertion into a vein of a patient to be used in haemodialysis treatments.

Multiple lumen catheters have been available for many years for a variety of medical purposes. It is only in recent years, however, that such catheters have been developed for use in haemodialysis. The general form of multiple lumen catheters goes back to as early as 1882 when Pfarre patented such a catheter in the United States under Ser. No. 256,590. This patent teaches a flexible dual lumen catheter which is used primarily for cleaning and drainage of, for example, the bladder, rectum, stomach and ear. In this type of catheterization, the catheter is introduced into an existing body orifice without the use of any puncturing needle or guidewire.

More recently, a catheter was developed and patented by Blake et al under U.S. Pat. No. 3,634,924. This 1972 patent teaches a double lumen cardiac balloon catheter which is introduced into a large vein and the balloon inflated to control the flow in the vein. The catheter can in fact be placed by using the balloon as a "sail" to move with the blood into or through the heart to a position where the catheter takes up its intended function. This patent uses two lumens and teaches a method of making a tip which involves the use of a plug and a wire which retains the shape of one of the lumens during formation of the tip in a moulding technique.

Further patents which teach multiple lumen catheters for general use include the following U.S. Pat. Nos. 701,075; 2,175,726; 2,819,718; 4,072,146; 4,098,275; 4,134,402; 4,406,656 and 4,180,068.

Vascular catheter access by surgical cut-down techniques has been known to the medical profession for many years and, in fact, can be traced back to the 17th century. However, it was only with the introduction of the Seldinger technique in 1953 or thereabouts that a new approach could be used to improve vascular access. This technique was taught in an article published by Seldinger resulting from a presentation made at the Congress of the Northern Association of Medical Radiology at Helsinki in June of 1952. The technique essentially involves the use of a hollow needle to make an initial puncture and then a wire is entered through the needle and positioned in the vessel. The needle is withdrawn and the catheter is entered perecutaneously over the wire which is later withdrawn. With this technique it became possible to make less traumatic vascular access and has now become the accepted method of performing access in numerous medical techniques. One of these techniques which has been the subject of much research and development, is haemodialysis.

Haemodialysis can be defined as the temporary removal of blood from a patient for the purpose of extracting or separating toxins therefrom and the return of the cleansed blood to the same patient. Haemodialysis is indicated in patients where renal impairment or failure exists, that is, in cases where the blood is not being properly or sufficiently cleansed, (particularly to remove water) by the kidneys.

In the case of chronic renal impairment or failure, haemodialysis has to be carried out on a repetitive basis. For example, in end stage kidney disease where transplanation of kidneys is not possible or for medical reasons is contra-indicated, the patient will have to be dialysed about 100 to 150 times per year. This can result in several thousand accesses to the blood stream to enable the active haemodialysis to be performed over the remaining life of the patient.

Towards the end of 1960, Dr. Stanley Shaldon and colleagues developed, in the Royal Free Hospital in London, England, a technique for haemodialysis by percutaneous catheterization of deep blood vessels, specifically the femoral artery and vein. The technique was described in an article published by Dr. Shaldon and his associates in the Oct. 14th, 1961 edition of the Lancet at Pages 857 to 859. Dr. Shaldon and his associates developed single lumen catheters having tapered tips for entry over a Seldinger wire to be used in haemodialysis. Subsequently, Dr. Shaldon and his colleagues began to insert both inlet and outlet catheters in the femoral vein and this was reported in the British Medical Journal of Jun. 19th, 1963. The purpose of providing both inlet and outlet catheters in the femoral vein was to explore the possiblity of a "self-service" approach to dialysis. Dr. Shaldon was subsequently successful in doing this and patients were able to operate reasonably normally while carrying implanted catheters which could be connected to haemodialysis equipment periodically.

Some use was made of a flexible dual lumen catheter inserted by surgical cut-down as early as 1959. An example of such a catheter is that of McIntosh and colleagues which is described in the Journal of the American Medical Association of Feb. 21, 1959 at pages 137 to 138. In this publication, a dual lumen catheter is made of non-toxic vinyl plastic and described as being inserted by cut-down technique into the saphenous vein to the inferior vena cava.

The advantage of dual lumen catheters in haemodialysis is that only one vein access need be affected to establish continued dialysis of the blood, because one lumen serves as the conduit for blood flowing from the patient to the dialysis unit and the other lumen serves as a conduit for blood returning from the dialysis unit to the patient. This contrasts with prior systems where either two insertions were necessary to place the two catheters as was done by Dr. Shaldon, or a single cathether was used with a complicated dialysis machine which alternately removed blood and returned cleansed blood.

The success of Dr. Shaldon in placing catheters which will remain in place for periodic haemodialysis caused further work to be done with different sites. Dr. Shaldon used the femoral vein and in about 1977 Dr. Uldall began clinical testing of a subclavian catheter that would remain in place. An article describing this was published by Dr. Uldall and others in Dialysis and Transplantation, Volume 8, No. 10, in October 1979. Subsequently Dr. Uldall began experimenting with a coaxial dual lumen catheter for subclavian insertion and this resulted in Canadian Pat. No. 1,092,927 which issued on Jan. 6, 1981. Although this particular form of catheter has not achieved significant success in the market-place, it was the forerunner of dual lumen catheters implanted in the subclavian vein for periodic haemodialysis.

The next significant step in the development of a dual lumen catheter for haemodialysis in U.S. Pat. No. 1,150,122 to Martin who produced a catheter which achieved some commercial success. The catheter avoided the disadvantages of the Uldall structure.

A subsequent development is shown in U.S. Pat. No. 4,451,252 also to Martin. This utilizes the well known dual lumen configuration in which the lumens are arranged side-by-side separated by a diametric septum. The structure shown in this patent provides for a tip making it possible to enter a Seldinger wire through one of the lumens and to use this wire as a guide for inserting the catheter percutaneously. Patents to this type of structure followed and include European Patent Application to Edelman published under No. 0 079 719, U.S. Pat. Nos. 4,619,643, 4,583,968, 4,568,329, and U.S. Pat. No. DES 272, 651.

There have been a number of problems associated with the manufacture of dual lumen catheters from extrusions in which the lumens are placed side-by-side and separated by a septum. A notable problem lies in the fact that the end or tip of the catheter has to be formed with a wire in one lumen by deforming the material from one side towards the center of the catheter. The wire will retain stored energy as it is displaced sideways to the centre of the tip so that as soon as the tip is removed from the mould, the wire will tend to return to an inline position thereby deforming the tip away from the center. Also, because the material forming the tipe is either obtained by inserting fillers or the like, it is of an asymmetric cross-section so that, on cooling, there will be shrinkage effects again tending to deform the tip. Because it is desirable to retain the tip in a concentric relationship with the axis of the catheter, these disadvantages have become noticeable in products made according to some of the aforementioned patents.

One approach to solving the problem of creating a tip is to be found in U.S. Pat. No. 4,543,087 to Sommercorn. This patent teaches the use of a separate moulded tip which is inserted into the end of an extrusion to provide the necessary flow paths. However, although the tip has resulted in significant commerical success, it does have the disadvantage that the tip must be inserted into the lumens with resulting discontinuity in the flow path of the return lumen because the blood must meet the end of the insert and pass into an opening through the insert which is of smaller cross-section than the lumen itself.

All of the above examples of haemodialysis catheters which are inserted over a "Seldinger" nine suffer from the disadvantages that they can not be used readily for intravenous injection of liquid medication. A person who is using haemodialysis therapy with a dual lumen catheter will have to receive a needle for intravenous injection and medication of this kind is required. It would be desirable that the catheter not only perform the function of haemodialysis, but also provide a facility for intravenous injection without further puncturing of the patient's veins. It is one of the objects of the present invention to provide a method of making such a catheter.

The present invention is also intended to provide a method of manufacture which improves the tip on the catheter so that it will have minimal tendency to deform after moulding and the resulting tip will then be symmetrical about the axis of the catheter.

The foregoing problems associated with haemodialysis catheters may in instances be specific to that treatment. However, the present invention, provides a method of making a catheter which has utility in other procedures. Accordingly, although the present description is directed to haemodialysis, such use is exemplary and it will be evident that catheters according to the invention may be made for in other procedures.

In one of its aspects the present invention provides a method of manufacturing a multiple lumen catheter with a tapered tip and an end aperture concentric with the main catheter body comprising the steps of providing a flexible elongated body extending about a longitudinal axis having a distal end and a proximal end, an outer wall and an integral septum defining first and second lumens, and a portion of the septum defining a third lumen extending along the longitudinal axis, the lumens extending from the proximal end to the distal end, inserting a straight wire in the third lumen to extend from the distal end of the body, inserting the distal end of the body in a conical tapered mould having a centrally located aperture to receive the wire, softening the distal end of the body in the mould such that the distal end deforms to a tapered shape, the outer wall of the body merging with the septum to close the first and seocnd lumens, and forming apertures in the outer wall between the inserters and the proximal end.

Thig and other aspects of the invention will now be described with reference to the accompanying drawings, in which.

The method of the invention will be described in detail with reference to a preferred embodiment to be used for haemodialysis. However the drawings and description are exemplary of the invention and unless otherwise stated, are not intended to be limited by its restraints of size and properties dictated by haemodialysis procedures.

Figure 1:
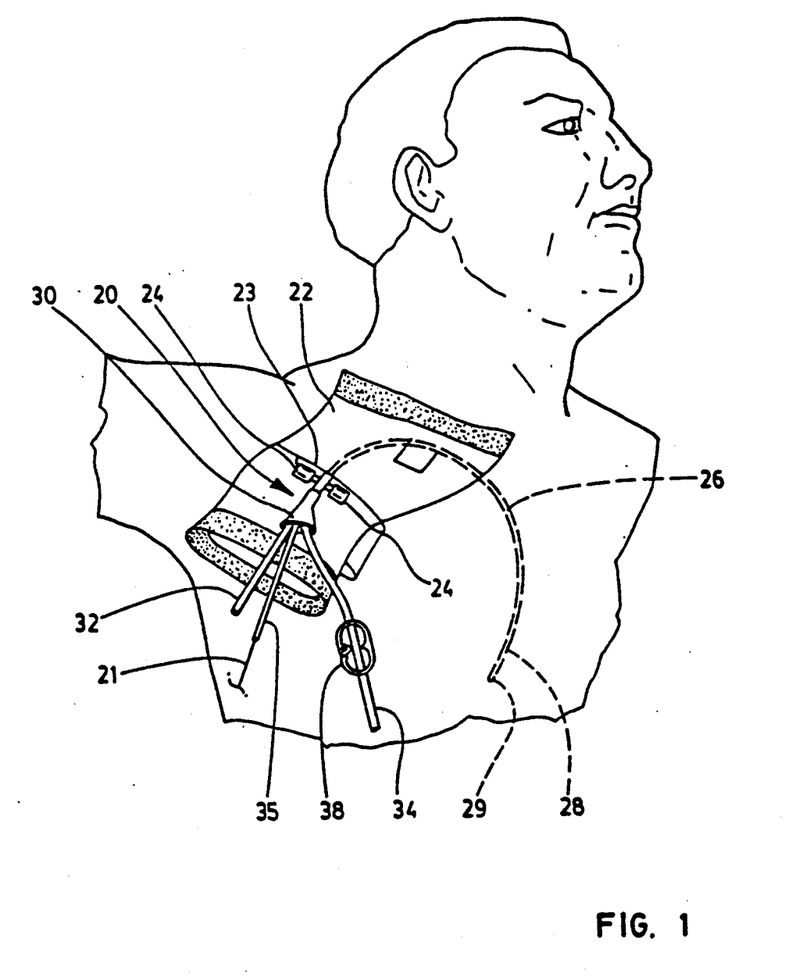
FIG. 1 is a diagrammatic view of a triple lumen catheter made according to a preferred embodiment of the method of to present invention, the catheter being shown inserted into the subclavian vein of a patient.

Reference is made first to FIG. 1 of the drawings which illustrates a triple lumen catheter, indicated generally by reference numeral 20, made according to a preferred embodiment of the present invention, and showing by way of example, a patient receiving the catheter in the subclavian vein using a Seldinger wire 21. The catheter is to be used for haemodialysis treatment and could of course also be entered in a similar fashion in the femoral vein.

The catheter 20 is secured to a conventional dressing 22 by an attachment fitting 23 having wing tabs 24, and the dressing 22, in turn, is secured to the skin of the patient. As shown, the catheter 20 passes through the dressing 22 and, as can be seen in broken outline, and elongate and flexible cylindrical body 26, formed of a polyurethane extrusion, is inserted through the skin and into the subclavian vein in the downstream direction. The catheter 20 has at its distal end 28 a conical tapered tip 29 which is described in greater detail below. The other end of the body 26 is a generally trident-shaped branching connector 30, which protrudes outwardly from and is secured by dressing 22. Cylindrical blood extraction and return tubes 32, 34 and an intravenous (IV) tube 35 are attached to the trident-shaped branching connector 30, a full description of which is provided below. For the moment it is sufficient to state that these tubes are connected to lumens running through the body 26.

Figure 2:
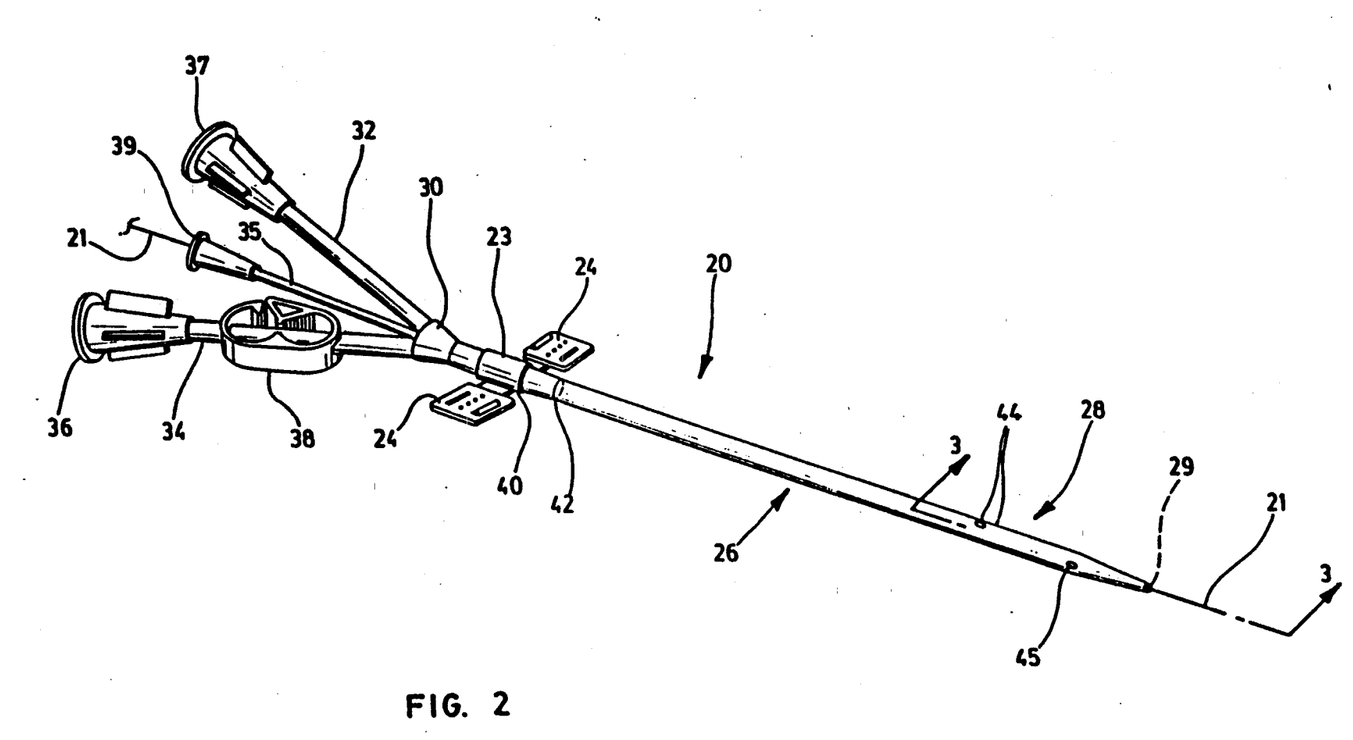
FIG. 2 is a diagrammatic perspective view of the catheter drawn to a larger scale than that used in FIG. 1.

FIG. 2 shows the catheter 20 in greater detail. The body 26 has at its proximal end the connector 30 for receiving the blood extraction and return tubes 32, 34. These tubes terminate at their outer ends in respective female luer fittings 36, 37 for connection to complementary male luer fittings (not shown) leading to a dialysis machine, and carry closure clamps 38 (one of which is shown) to selectively close the tubes.

The IV tube 35 terminates at its outer end in a luer lock fitting 39 for receiving a syringe or male luer lock connector.

The wing tabs 24, sometimes known as suture wings, are formed integrally with a central tubular portion 40 which can rotate on the body 26 and is retained in place by a shoulder on the end of the connector 30 and a second shoulder in a reinforcing portion 42 so that the catheter 20 can be rotated relative to the tabs 24. This rotation is sometimes necessary after insertion of the catheter 20 to re-orientate intake side apertures in the distal end 28 if the apertures happen to be occluded by engagement with the wall of the vein. Details of the apertures are provided below.

As will be described, the reinforcing portion 42 is blended into the body 26 over the length of the portion and assists in strengthening the catheter to minimize the likelihood of kinking. Also, the portion 42 assists in sealing the puncture site where the catheter enters the patient.

As will be described in more detail with reference to subsequent views, the tube 35 is aligned with a central lumen to permit the Seldinger wire 21 to pass through the catheter. The wire exits at tip 29 which is essentially conical so that the catheter can slide over the wire and into the patient during insertion. The extraction and return tubes 32, 34 are linked at connector 30 with lumens in the body 26 to connect with respective groups of side apertures 44, 45 (some of which can be seen in this view) near the distal end of the catheter 28. As a result, when inserted and in use, blood can be removed and returned in a closed loop with a haemodialysis machine using the tubes 32, 34. Between treatments the tube 35 is available for intravenous infusion of liquid medicaments.

Figure 3:
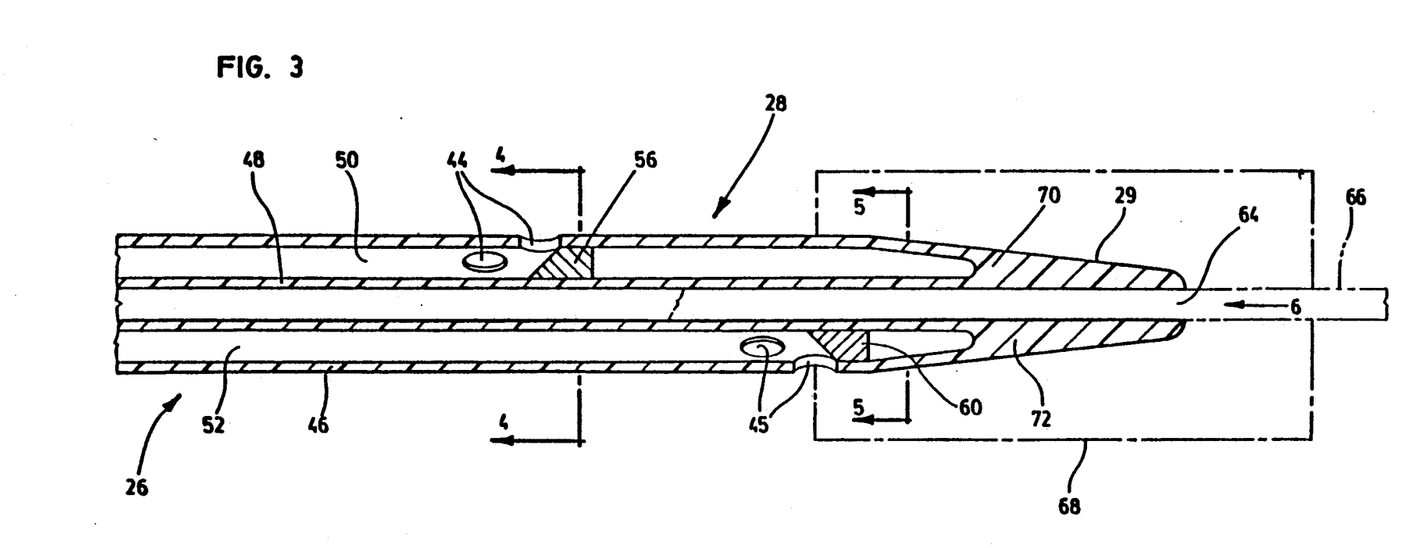
FIG. 3 is an enlarged sectional view of the distal end of the catheter of FIG. 1 drawn on line 3—3 of FIG. 2.
Figure 4:
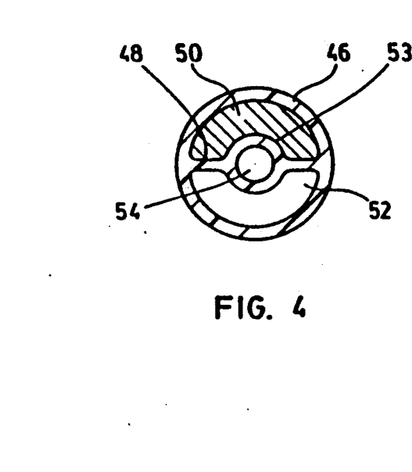
FIGS. 4 and 5 are enlarged sectional views taken on the lines 4—4, 5—5, of FIG. 3, respectively, and showing complete sections.
Figure 5:
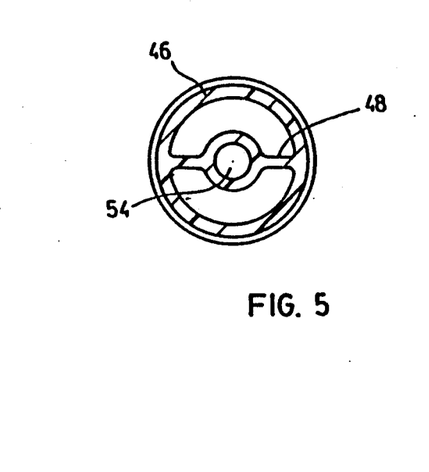

Reference is next made to FIGS. 3 to 6 of the drawings which illustrate the distal end 28 including tip 29. The body 26 comprises an outer wall 46 and an integral septum 48 extending diametrically across the body 26 and defining an extraction lumen 50 and a return lumen 52, both lumens being generally C-shaped in cross-section and extending from the proximal end towards the distal end. As best seen in FIG. 4, a bulbous middle portion 53 of the spectum 48 projects into the lumens 50, 52 and contains the intravenous (IV) lumen 54 which extends along the longitudinal axis of the body portion 26 from the proximal end to the distal end. This lumen is an extension of the IV tube 35 and is proportioned in this embodiment to receive a 0.038 inch diameter Seldinger wire.

The extraction lumen 50 is blocked short of the tip 29 by a first insert 56 which is formed of polyurethane and bonded in place using a suitable solvent such as cyclohexanone. Extraction apertures 44 are provided in the outer wall 46 of the cylindrical portion 26, just short of the insert 56, to permit blood to flow from the patient's vein into the extraction lumen 50 and thus through the connector 30 to the extraction tube 32 and the dialysis machine. It should be noted that the apertures 44 are conveniently circular but may be of any suitable shape or size including scaphoid. Also, further extraction apertures may be provided around the lumen 50 as required consistent with the aperture nearest the tip being immediately adjacent the insert 56 to minimize dead spaces.

The return lumen 52 is similarily blocked by a second insert 60 immediately adjacent the last of several return apertures 45. This last aperture is positioned closer to the tip 29 than is the last of the intake apertures 44 in the extraction lumen 50 to minimize the risk of cross flow as returning blood finds its way back into the lumen 50. Although some cross-flow is not critical, excess cross-flow will extend the time needed for haemodialysis.

Figure 6:
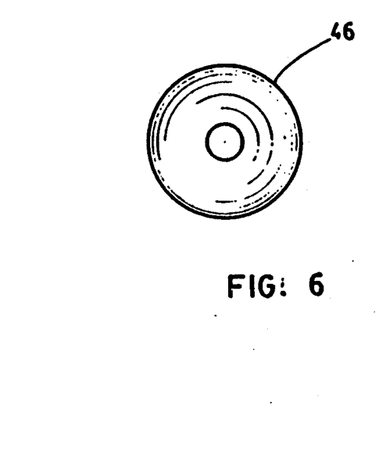
FIG. 6 is an end view of the catheter in the direction generally of arrow 6 of FIG. 3.

As can be seen in FIGS. 3 and 6, the tip 29 is smoothly rounded at the end 28 of the catheter and tapered gently to facilitate insertion of the catheter 20 into a patient. As mentioned previously, the catheter is intended to be used with a Seldinger wire. In this embodiment the tapered tip 29 is concentric with the axis with the body 26 and of the lumen 54. Accordingly, the centrally located lumen 54 extends to the tip 29 and terminates at a circular IV aperture 64.

The catheter 20 is made from a length of cylindrical polyurethane extrusion forming the cylindrical body 26. The extrusion is cut to the required length and the ends formed by further operations. The formation of the tapered tip 29 will be described with reference firstly to FIG. 3, followed by a description of the formation of the connector 30.

Before shaping the tapered tip 29, the inserts 56, 60 are positioned and affixed in the respective lumens 50, 52, as shown in FIG. 3. The inserts are shaped to the cross-section of the lumens and affixed as previously described. A cylindrical wire 66 (shown in chain dotted outline), of corresponding diameter to that of the guide wire 21 (FIG. 2), is inserted through the IV lumen 54 to extend from the distal end of the tubing which is then located in a conical tapered mould 68 (shown in chain-dotted outline in FIG. 3). The extrusion is heated by R. F. and as it softens it is pushed into the mould such that the outer wall 46 and the septum 48 merge at the tip 29. The end of the body assumes a conical tapered shape with a radiused end and the material masses in the lumens 50, 52 forming ends 70, 72. The IV lumen 54 retains its internal shape because it is supported on the wire 66. The now tapered tip is cooled to some extent and then removed from the mould 68 and allowed to cool further and harden.

The deformation of the tip results in a thickening of the outer wall 46 and septum 48 to provide a concentration of material substantially exceeding the concentration of material in the main catheter body, and this facilitates insertion of the catheter.

Because the wire 66 is not deflected at any time from its normal straight condition during the moulding operation, there is no energy stored in the wire and consequently there is no tendency for the wire to deflect the tip from the desired orientation after removal from the mould 68.

The wire can therefore be left inside the tip during cooling. The apertures 44, 45 are then cut or otherwise formed in the outer wall 46 of the body 26. Also, because the extrusion is symmetrical about the wire, the deformed material at the tip will move evenly to both sides of the central spectum. The resulting similar masses at ends 70, 72 of the lumens will cool and shrink equally so that the tip will remain concentric about the central or IV lumen 54. This will result in a well formed tapered tip.

The method of manufacture of the trident-shaped branching connector 30 and reinforcing portion 42 will next be described with reference to FIGS. 7 to 12. The figures are arranged in order of the steps used in the manufacture and it will be seen in FIG. 7 that the extruded body 26 has received a short sleeve 71 of polyurethene and preferably the same colour as that used for the body. The sleeve 71 is a snug fit on the cylindrical body 26 and after positioning on the body, the assembly is moved into a heated mould 73 which has a frustro-conical interior wall 75 designed to deform the sleeve 71 to create the blended reinforcing portion 42 shown in FIG. 2. If preferred, suitable shaped mandrels can be placed inside the lumens of the body 26 to ensure that the lumens are not deformed while the collar is shaped in the mould 73. The sleeve 71 is heated and the body pushed into the heated mould 73 so that material flows to the desired shape.

Figures 7, 8:
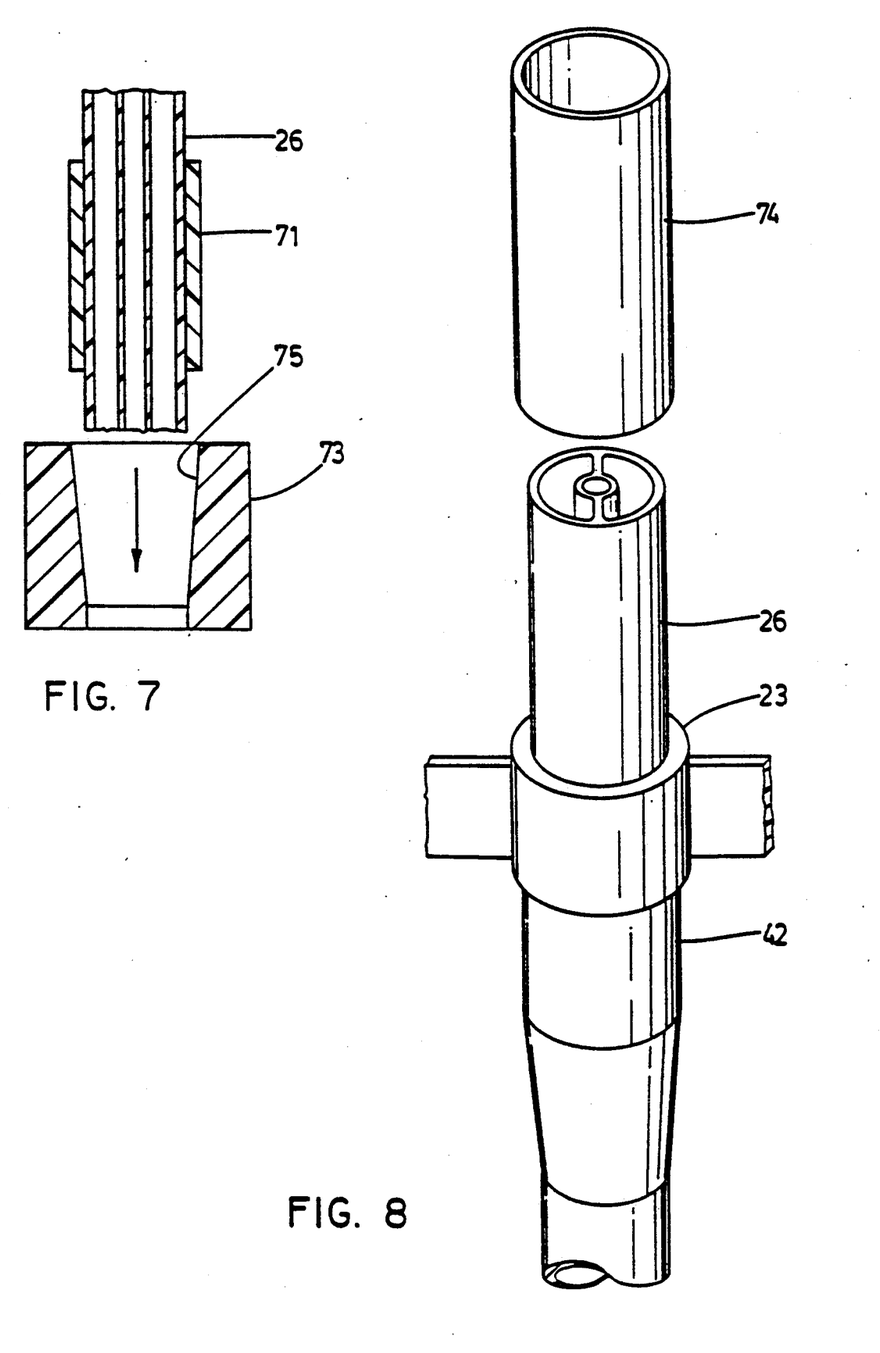
FIGS. 7, 8, 9, 10 and 11 are diagrammatic perspective views of an end of the catheter showing the various steps in the manufacture of the trident-shaped branching connector and associated parts.

The upper edge of the sleeve 71 (as drawn) forms a shoulder and is positioned for engagement with the attachment fitting 23 shown in FIG. 2 to locate this fitting longitudinally on the body.

After completing the process illustrated in FIG. 7, the fitting 23 is slipped over the end of the body 26 and into engagement with the sleeve 71. The fitting is a loose fit so that it can rotate freely on the body 26. The positioning can be seen in FIG. 8 which also shows the completed reinforcing portion 42 and how it blends into the body 26.

Figure 9:
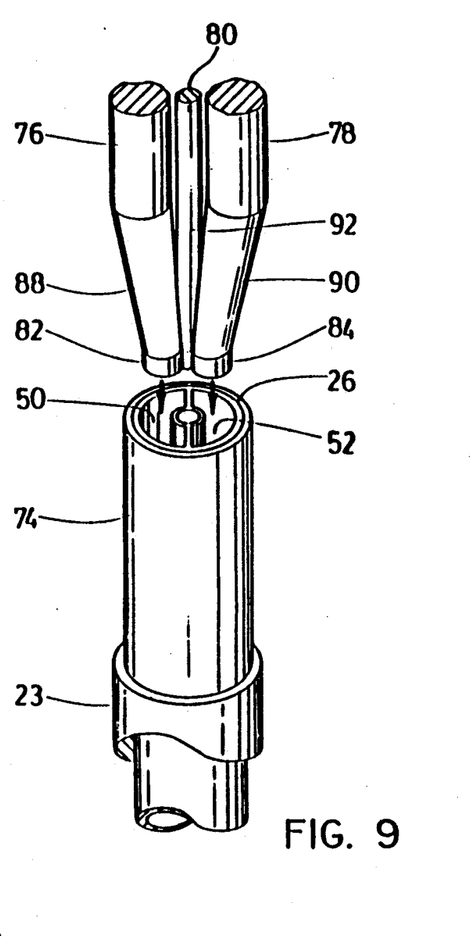

Next another sleeve 74 is engaged over the end of the tube 26 and, if the first sleeve has been positioned correctly, the sleeve 74 will be positioned so that its trailing end becomes flush with the end of the body 26 as shown in FIG. 9. The sleeve 74 should not be pushed tightly against the attachment fitting 23 in order to provide clearance of free movement of the fitting. With the sleeve in position, a set of deforming mandrels are brought into play as seen in FIG. 9. There are three mandrels, one for each of the lumens. The two outer mandrels 76, 78 are mirror images of one another and positioned about a central mandrel 80. The intent of the mandrels is to form the corresponding lumens to have conical outer portions for receiving shaped ends of the tubes 32, 34 and 35 (FIG. 2) as will be described with reference to FIG. 12.

The mandrels 76, 78 have respective leading ends 82, 84 which are proportioned simply to provide location as they enter corresponding lumens 50, 52 and similarly, a leading portion 86 on the mandrel 80 is proportioned to engage the central lumen 54. The leading portions 82, 84 and 86 blend into respective conical portions 88, 90 and 92 which are arranged to complement one another so that the cones will flair outwardly to receive the tubes. Of course for simplicity of engagement, each of the mandrels is supported from shanks which are arranged in parallel so that the mandrels can be brought into the extrusion longitudinally and deformation will take place simply because the conical portions are larger than the lumens and the material around the lumens will be forced outwardly under the influence of heat provided by heating the mandrels. The second sleeve 74 supports the extrusion which is itself insufficient to support this deformation as the size is increased.

Figure 10:
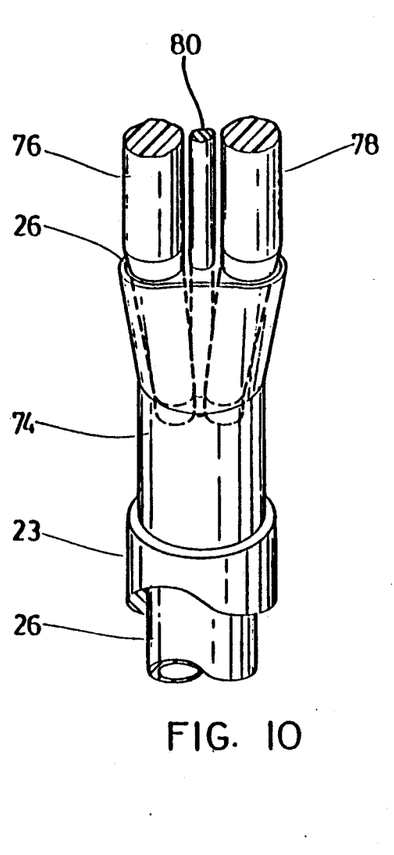
Figure 11:
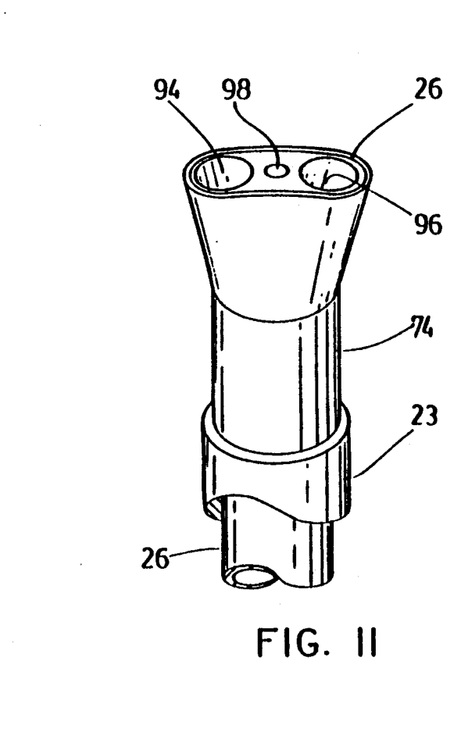

It will be seen in FIG. 10, that after the mandrels are engaged, the sleeve and contained portion of the extrusion are expanded and, after completion, the appearance will be as shown in FIG. 11.

Figure 12:
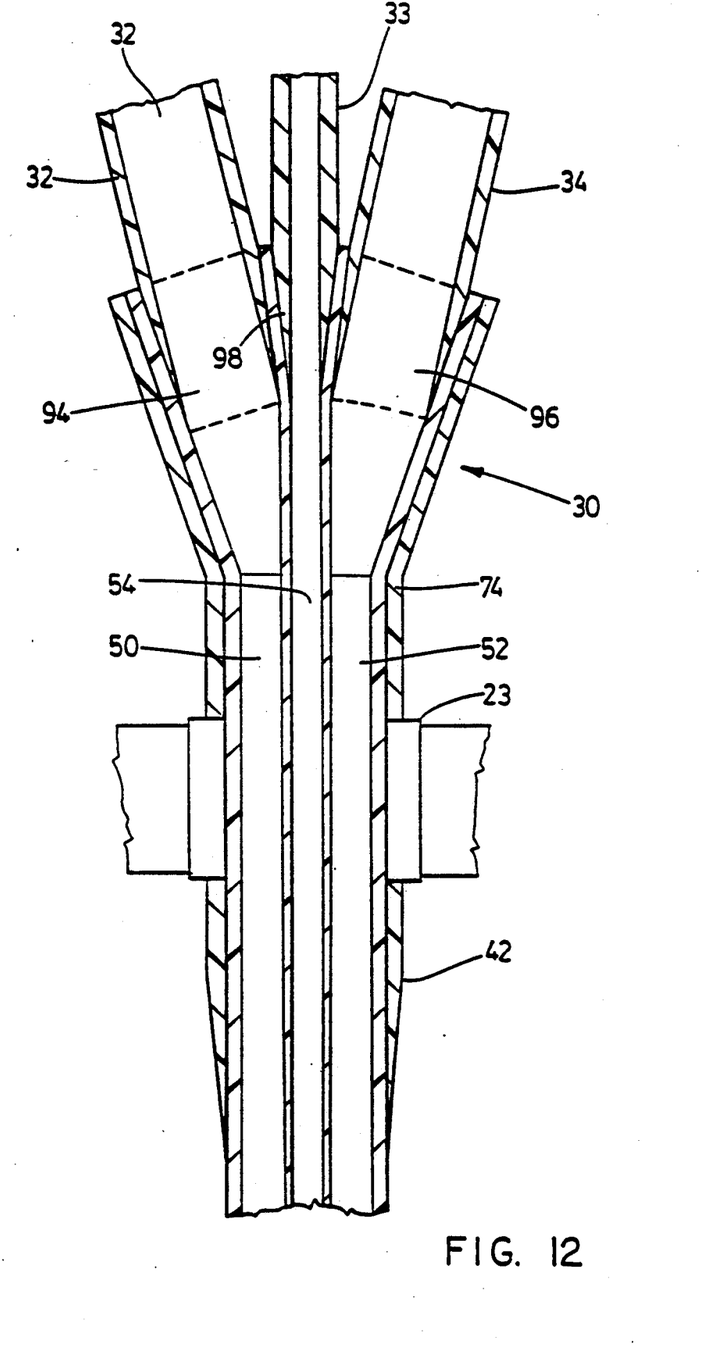
FIG. 12 is a sectional view of the connector after assembly.

Reference is next made to FIG. 12 which shows the engagement of the tubes 32, 34 and 35 in the connector 30. These tubes have their engagement ends deformed to thin the wall and this is done by conical deformations so that the outer surface of the tubes are slightly conical to engage the corresponding internal cones 94, 96 and 98 shown in FIG. 11 and formed by the use of the mandrels. It will be seen in FIG. 12 that the result in assembly is compact, and provides a relatively smooth internal surface to minimize the risk of blood damage caused by turbulence as blood flows through the tubes and associated lumens 32, 34 and 50, 52. Similarly, the tube 35 is engaged so that there is no interference with the Seldinger wire which will slide freely through this tube an lumen 54.

The tubes are attached in the connector 30 using a suitable solvent in a similar fashion to the attachment of the plugs 56, 60 described with reference to FIG. 3.

It is of course possible to make the assembly starting with the trident shaped structure and then add the fitting 23 from the distal end of the body before ending by adding and forming sleeve 71.

In use, as mentioned above, the catheter 20 is inserted such that it points downstream in the patient's vein, that is, the extraction aperture 44 are upstream of the return apertures 45, which, in turn, are upstream of the IV tip aperture 64. When a treatment is in progress the extraction tubes 32, 34 are connected to a dialysis machine which draws blood through the extraction lumen 50 and returns it through return lumen 52 in a similar manner to a conventional dual lumen cannula. Between blood treatments the lumens may be filled with a heparin solution to prevent them from being filled with clotted blood. However, if the patient requires medication or is required to give blood between treatments, the IV lumen 54 may be used. This avoids the trauma and discomfort of the inserting a further needle or catheter into the patient and does not disturb the heparin lock.

Between uses the third lumen may be filled with a relatively small volume of heparin or may be occupied by cylindrical solid and flexible patency obturator, similar to guide wire 21. This obturator prevents the entrance of blood into the lumen and thus eliminates the need for heparin in the third lumen. Generally, it will be easier to keep the third lumen free of blood due to its smaller cross-section, regular shape and absence of side holes.

In addition to this advantage the centrally located lumen offers considerable advantages for insertion and removal of the catheter. As there are no sideholes in the lumen, "J" ended guide wires may be used without the possibility that the guidwire will exit through a sidehole, rather than the end aperture. In addition, because it is easier to keep the smaller lumen free of clotted blood, it should be possible to use a guidewire to replace a catheter which has clotted blood in the blood lumens without dislodging any blood clots which may have accumulated in the blood lumens. This would be done by first entering the Seldinger wire into the third lumen of the catheter in place in the vein, withdrawing this catheter over the wire leaving the wire in place, and then using the wire to guide a replacement catheter over the guide wire.

The exemplary catheter described with reference to the drawings does not have the proportions of a haemodialysis catheter. As mentioned previously, the description is exemplary and in practice, if the catheter is to be used in the subclavian vein it will have proportions as follows. The central lumen will have a diameter of about 0.04 inches to receive a Seldinger wire of diameter 0.038 inches or 0.036 inches. The walls about the central lumen and forming the septum will be about 0.010 inches in thickness and will blend into the outer wall which is about 0.013 inches in thickness. The outer diameter of the body 26 will be 0.149 inches and this will give an area available for blood flow in the lumens of about 0.0048 square inches. The flow rate will be approximately 237 milliliters per minute using accepted pressures to drive the blood through the lumens.

Clearly catheters can be made with a variety of proportions depending upon the use and structures defined by the claims and incorporating the description are within the scope of the invention.

Figure 13:
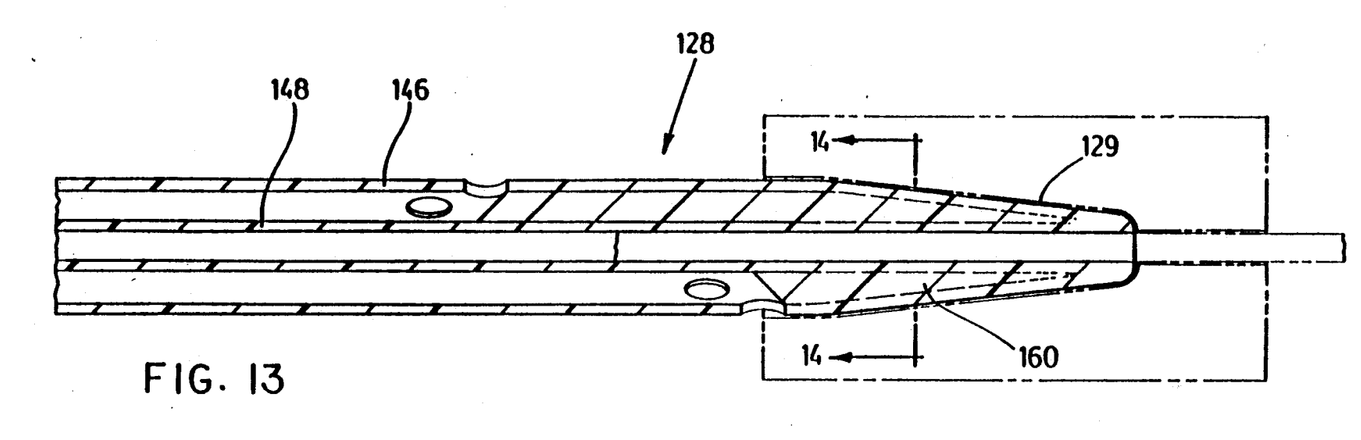
FIG. 13 is a view similar to FIG. 3 of the distal end of another embodiment of the present invention.
Figure 14:
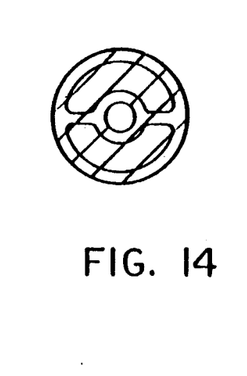
FIG 14 is a sectional viesw taken on line 14—14 of FIG. 13.

The tip structure shown in FIG. 3 can be made in a number of ways. An alternative is shown in FIGS. 13 and 14. For ease of reference the reference numerals used in relation to these figures correspond to those used above prefixed with the numeral 1. The distal end 128 and tip 129 of a catheter has inserts 156, 160 which extend to fill the unused portions of the extraction and return lumens. The inserts are entered in the lumens 150, 152 and may be affixed therein by a solvent. When the end 128 is heated in the mould 168 the inserts 156, 160 are softened and deformed and the outer wall 146 collapes to merge with the septum 148. The leading ends of the inserts 156, 160, also merge with the septum 148, as represented by the ghost outlines in FIG. 13 and 14. The resulting catheter has an appearance similar to the catheter described above but with a stiffer leading end.

It will be evident that the form of the inserts can vary. For instance the ends originally near the end 128 could be thinned to allow for easier deformation of the extrusion into the shape shown in FIG. 13.

Figure 15:
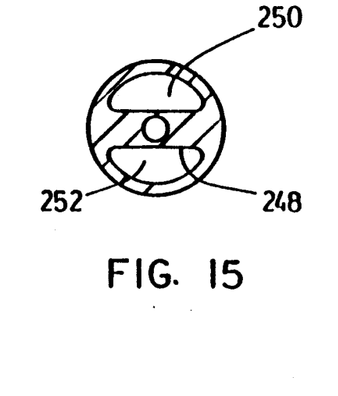
FIG. 15 is, a sectional view of a further embodiment of the catheter.

The catheters illustrated and described above feature septums having a bulbous middle portion to accomodate the IV lumen. However, the catheter of the invention is not limited to this particular cross-section and FIG. 15 shows an alternative cross-section. For ease of reference the numerals used in relation to this figure correspond to those used to describe the preferred embodiment prefixed with the numeral 2. The catheter illustrated has a septum 248 with planar sides such that the extraction and return lumens 250, 252 have a D-shaped cross-section. This thicker septum 248 requires the use of more material to form the catheter and also reduces the ratio between the cross-sectional area of the extraction and return lumens and the cross-sectional area of the catheter. However there may be uses above where this cross-section is advantageous, for instance where the outer diameter of the catheter body is less critical then it is when used in a vein for haemodialysis.

Figure 16:
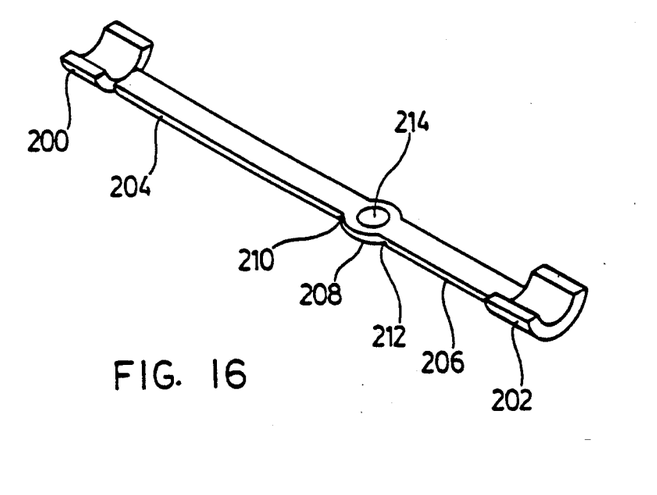
FIG. 16 is a perspective view of a plug for use in making yet another embodiment of the catheter.

Reference is now made to FIG. 16 to describe a moulded plug of polyurethane for use in making tips. This plug has end pieces 200,202 shaped to fit snugly in the lumens 50, 52 (FIG. 3). The end pieces are attached to respective spacers 204,206 which depend from a hub 208 at respective weakened joints 210,212. The hub has a central opening 214 matching the third lumen 54 so that the wire used in moulding can be used to locate the hub centrally.

Figure 17:
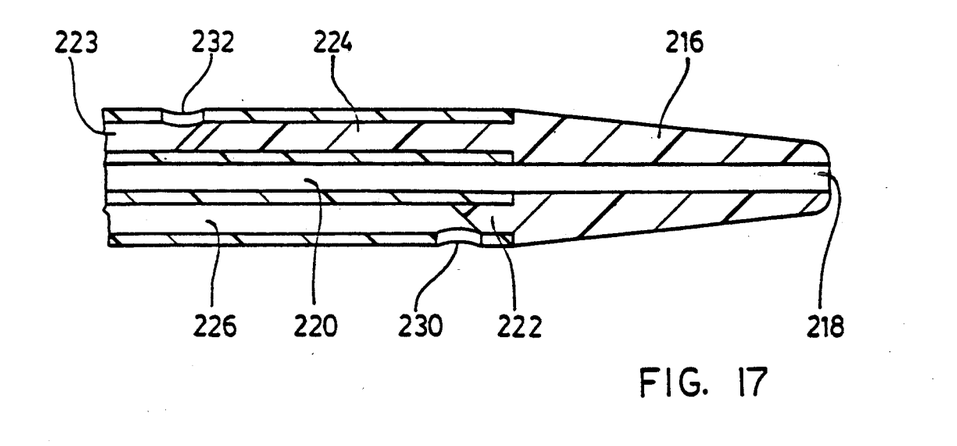
FIG. 17 is a sectional view of still another embodiment of the catheter and using a separate bonded tip.

The procedure, when using the plug of FIG. 16, is to first bend the spacers 204,206 about the joints 210,212 so that the end pieces 200,202 come together for insertion in the end of the extruded body 26. The pieces are pushed home with solvent until the hub 208 meets the end of the body. The pieces 200,202 will then automatically be in the required positions controlled by the lengths of the spacers 204,206. Moulding then proceeds as before so that the hub and adjacent parts of the spacers will become integral portions of the tip. A further embodiment is shown in FIG. 17. This structure includes a separate moulded tip 216 preferably of polyurethane, which is engaged in and bonded to the end the extrusion. The tip 216 has an outer conical form and defines a central opening 218 forming a continuation of the third lumen 220. A pair of extensions 222, 224 are shaped to fit in the respective lumens 226, 228 and have lengths to match the positions of the apertures 230, 232 in the side wall of the lumens. The ends of the extensions are preferably shaped to meet the apertures and complement the natural flow patterns so that dead spaces wil be minimized if not eliminated.

The structure shown in FIG. 17 can also be partly formed by heating in a mould to blend the joint between the tip and the extrusion. This technique can also be used to part form the assembly to improve the tip if necessary.

The method of shaping the end is described as utilizing radio frequency heating devices to soften the plastic material. This is intended to be illustrative of a softening technique, and other techniques, for example, the use of electrical heating elements, are equally effective.

Figure 18:
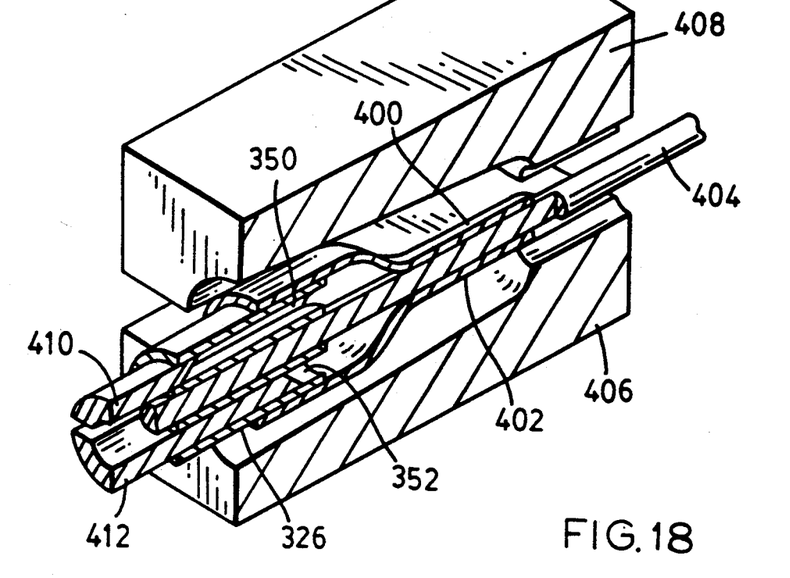
FIG. 18 is a sectional view illustrating an alternative method of manufacturing a tip according to the invention.

The third method of manufacturing the tip is illustrated in FIG. 18. Numerals corresponding to those used in FIG. 3 will be repeated with a prefix "3".

In this embodiment, a body 326 receives an extension piece 400 shaped to fit roughtly on the end of the body and having a projection 402 of the shape needed as a continuation of the cental aperture of third lumen. The parts are located relative to one another by a central rod 404 within two halves 406, 408 of a heated dye shaped to correspond to the tip shape shown in FIG. 3. This shape can of course be modified to provide varying ends on the catheter depending upon the desired configuration.

The body 326 receives first and second mandrels 410, 412 shaped to fit within the lumens 350, 352 and positioned so that material flowing under the influence of the heat will engage with the ends of the mandrels in a fashion corresponding to the plugs 56, 60 shown in FIG. 18. The result will be continuous material from the distal end of the catheter to the ends of the mandrels 410, 412. The shaping can be seen in FIG. 3 but without the spacing between the plugs 56, 60 and the solid end of the catheter.

Under the influence of heat, the material of the body 326 and extension 400 will flow and be shaped by the closing dye halves 406, 408. The necessary quantity of material required to complete the shape can be augmented by the provision of plugs in the lumens 350, 352 of a material which will also flow under the influence of heat. However with some care in design, it is possible to complete the tip without the use of these plugs.

The structure shown in FIG. 18 has the advantage that the extension 400 can be of any durometer hardness required consistant of course with the material matching that of the body 326. Consequently it is possible to create a distal end on the tip having different characteristics from the main body. The very end of the catheter can be quite soft so that when it is inserted, it will have minimal strength and therefore reduce the risk of damage to the wall of the vein after insertion. Such a tip may well make it possible to leave the catheter in place for longer periods than would be possible with a tip having a stiff end.

Figure 19:
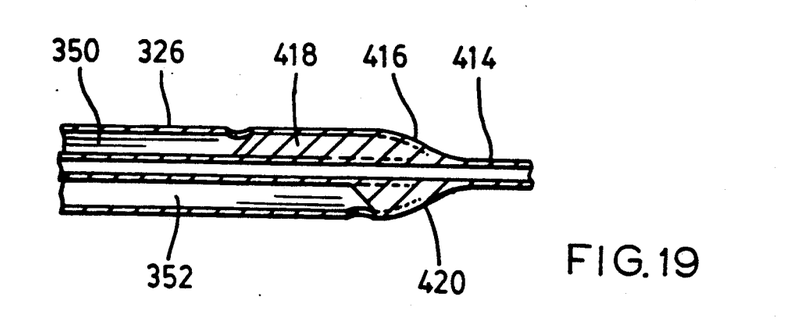
FIG. 19 (drawn adjacent FIG. 15) is a side view of a tip made using the method illustrated in FIG. 18.

Reference is now made to FIG. 19 which illustrates a further embodiment of tip made using the method of FIG. 18. As mentioned, the mould halves can be of different shapes since lumen 350 can be closed further from the tip than lumen 352. However the shapes chosen to make the structure in FIG. 19 provide a cylindrical central extension 414 made from a part similar to that identified as 402 in FIG. 18. There is a transition zone defining a shoulder 416 where the extension 414 blends smoothly into the body 326. In this embodiment, to provide sufficient material to block the lumens 350, 352, plugs 418 and 420 are provided and these flow into the material around them as indicated by the broken outline at the shoulder 416. With a suitable selection of material it is possible to provide the extension 414 with significantly different physical characteristics from the body, notably it can be made of soft material which will have very little effect on the inner wall surface of a vein. Similarly, the strength at the shoulder can be changed by using inserts of soft material or even providing plugs rather than inserts in the manner described with reference to FIG. 3.

Structures such as shown in FIGS. 3, 13, and 19 are exemplary of tips which are tapered. Some are frustroconical whereas others tend to have a shoulder such as that shown in FIG. 19. However, functionally they are all tapered since they will dilate tissue as they are moved along a Seldinger wire into position in a patient. For this reason, in the terminology of this application, the word "tapered" is intended to include any structure at the end which is capable of such dilation to facilitate engagement over a Seldinger wire.

It will be appreciated that various other modifications may be made to the catheter, and to the processes for making parts of the catheter as described, without departing from the scope of the invention, for example, the material used to form the tube and inserts may be any suitable medical grade thermoplastic. Also, the positioning of the apertures and the number of apertures is to some extent a matter of choice. Also, the length of the conical tip can be varied to include apertures in the wall of the tip. While such a structure is more complicated to make, the flow pattern would be advantageous.

Although methods of making catheters have been described in use in haemodialysis in a subclavian vein it would also be appreciated that it can be used in both femoral and jugular veins, and can also be used in other blood treatments including apheresis, haemoperfusion and non-blood related treatments involving nutrition and drug therapies.

We claim:

1. A method of manufacturing a multiple lumen catheter with a tapered tip and an end aperture concentric with the main catheter body comprising the steps of:
   providing a flexible elongate body extending about a longitudinal axis having a distal end, a proximal end, an outer wall, a septum extending between spaced points on the outer wall to define first and second lumens, and a third lumen defined about said axis in a central portion of the septum and extending along the longitudinal axis, the lumens extending from the proximal end to the distal end;
   inserting a straight wire into the third lumen to project centrally from the distal end of the body;
   inserting the distal end of the body into a tapering mould having a centrally located aperture to receive the wire;
   softening the distal end of the body in the mould such that the distal end deforms to a tapered shape, the outer wall of the body merging with the septum to close the first and second lumens; and
   forming openings in the outer wall communicating with the first and second lumens adjacent the distal end.

2. A method of manufacturing a multiple lumen catheter as claimed in claim 1 in which inserts are affixed in the first and second lumens, between the locations for the openings in the outer wall and the distal end and immediately adjacent the locations where the respective openings are to be formed.

3. A method of manufacturing a catheter as claimed in claim 1 and further comprising the steps of:
   providing a first cylindrical sleeve and positioning the sleeve on the outer wall at a selected location near the proximal end of the said elongated body and attaching the sleeve to the outer wall;
   positioning a collar having wing tabs extending therefrom over the proximal end of the body and locating said second collar at the proximal end of said first collar;
   providing a second cylindrical sleeve and positioning this sleeve on the proximal end of the outer wall so that the proximal end of this sleeve and the proximal end of the body are substantially flush;
   providing three mandrels having substantially conical ends adapted to fit into the respective lumens of the catheter;
   heating the mandrels to predetermined temperature;
   inserting the mandrels into the lumens for a period sufficient to deform the ends of the lumens together with the second sleeve into conical portions so that the end of the catheter becomes substantially trident-shaped; and
   removing the mandrels after predetermined cooling period so that the trident-shape is permanent.

* * * * *